United States Patent [19]

Ronnmark

[11] 4,031,896
[45] June 28, 1977

[54] SURGICAL SUCTION SETS

[75] Inventor: Per Magnus Lennart Ronnmark, Gislaved, Sweden

[73] Assignee: Molnlycke AB, Gothenburg, Sweden

[22] Filed: Oct. 17, 1975

[21] Appl. No.: 623,500

[30] Foreign Application Priority Data

Oct. 18, 1974 Sweden .............................. 7413157

[52] U.S. Cl. .............................................. 128/276
[51] Int. Cl.² ........................................ A61M 1/00
[58] Field of Search ... 128/276, 240, 350, 277–278, 128/240–241, 348

[56] References Cited

UNITED STATES PATENTS

| | | | |
|---|---|---|---|
| 3,528,427 | 9/1970 | Sheridan | 128/350 |
| 3,889,657 | 6/1975 | Baumgarten | 128/276 |

*Primary Examiner*—G.E. McNeil
*Attorney, Agent, or Firm*—Lerner, David, Littenberg & Samuel

[57] ABSTRACT

A surgical suction device is provided for removing fluid from a wound which device is adapted to be connected to a suction pump by a hose pipe. The device includes a tubular handle and an inner tube extending from one end of said handle. The inner tube is provided with a suction opening at one end and an open tip at its other end. An outer tube surrounds the inner tube to form an annular space therebetween with the inner and outer tubes being movable relative to each other. The outer tube is telescoped over a portion of the handle and includes an aperture normally aligned with an aperture formed in the handle for controlling the suction functions. A plurality of openings is also formed in the space for quickly removing large quantities of fluid from a wound. At one end of the outer tube there is provided a tapered section having a suction opening for contacting the wound and a seat member at its other end. The open tip of the inner tube is movable into and out of contact with the seat member of the tapered section so that when they are in contact, a single tube suction function is obtained, and when they are out of contact, a sump suction function is obtained.

10 Claims, 3 Drawing Figures

SURGICAL SUCTION SETS

FIELD OF THE INVENTION

The present invention relates generally to surgical suction devices, and specifically to an improved surgical suction device which may be operated to function either as a single tube suction device or a sump suction device at an operation where it is required to remove blood, mucus, and other undesirable liquids from operating wounds.

BACKGROUND OF THE INVENTION

Present surgical suction devices for removing fluid from a wound typically include a handle which is adapted to be connected to a hospital suction pump by a hose pipe. The handle is employed to manipulate the surgical suction device, and the suction is controlled by control apertures formed in the handle. The handle is connected to a tube, the tip of which can be provided with different types of caps and nozzles to perform different types of suction functions. In addition, there is presently a number of surgical suction devices on the market wherein the tube is bent at a particular angle in order to be suitable for a particular type of operative incision. Accordingly, present surgical suction devices are not completely satisfactory, since the tube nozzles must be changed in order to perform different types of surgical suction functions. For example, one type of nozzle must be employed if the suction device is to function as a single tube suction device and a different type of nozzle must be employed if the surgical device is to function as a sump suction device. The sump suction device is normally required during an operation where it is necessary to quickly remove large quantities of blood, mucus, and other undesirable fluids from the operating wounds. However, since present surgical suction devices require that the nozzles be changed, much valuable operating time is lost. In addition, it is also undesirable that in present surgical suction devices, the tubes are permanently bent or deformed for a particular type of incision so that many different surgical suction devices are required, each being bent or deformed at a different angle for a particular type of incision.

Broadly, it is an object of the present invention to provide an improved surgical suction device which overcomes one or more of the aforesaid drawbacks. Specifically, it is within the contemplation of the present invention to provide an improved surgical suction device which is constructed to function as a single tube suction device or a sump suction device by a simple adjustment.

It is a further object of the present invention to provide an improved surgical suction device which is flexible and may be adjusted to different angles in accordance with the operative incision being performed and, therefore, may be used for any type of operation and may be adjusted while the operation is being performed.

SUMMARY OF THE INVENTION

Briefly, in accordance with the principles of the invention, an improved surgical suction device is provided which includes a tubular handle, and an inner tube extending from one end of the handle and having a suction opening at one end and an open tip at the other end thereof. An outer tube surrounds the inner tube to form an annular space therebetween with the inner and outer tubes being movable relative to each other. The outer tube is telescoped over a portion of the handle and includes an aperture which is normally aligned with an aperture formed in the handle to control the suction opening of the inner tube. A plurality of openings is formed in the space for quickly removing large quantities of fluid from an operating wound. At one end of the outer tube, there is provided a tapered section having a suction opening at one end and a seat member at the other end thereof. The tip of the inner tube is movable into and out of contact with the seat member so that when they are in contact, a single tube suction function is obtained, and when they are out of contact, a sump suction function is obtained.

In addition, the outer tube includes a flexible tube connected to the handle, and the inner tube includes a flexible tube reinforced with a non-flexible wire so that the inner tube and outer tube may be deformed and retain their new shape. Further, the outer tube is rotatable relative to the handle to displace the handle aperture relative to the outer tube aperture and to thereby control the suction functions.

In this manner, the improved surgical suction device of the present invention avoids the need for the changing of nozzles in order to perform different types of suction functions. In addition, the improved device of the present invention avoids the need for maintaining a plurality of devices bent at different angles for the different types of incisions to be performed. The device of the present invention achieves these objects in a simple and efficient manner, while maintaining an inexpensive construction.

BRIEF DESCRIPTION OF THE DRAWINGS

Further objects, features, and advantages of the present invention will become apparent upon the consideration of the following detailed description of a presently-preferred embodiment when taken in conjunction with the accompanying drawings, wherein.

DETAILED DISCUSSION OF PREFERRED EMBODIMENT OF THE INVENTION

Figure 1:
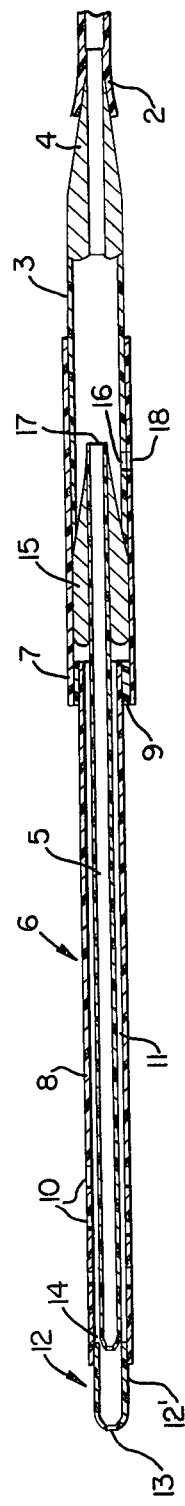
FIG. 1 is a longitudinal section of a surgical suction device in accordance with the present invention in its single tube suction position.
Figure 2:
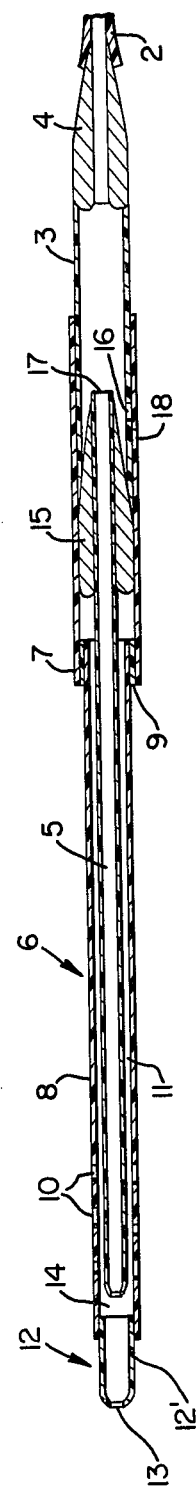
FIG. 2 is a longitudinal section of the device of the present invention in its sump suction position.
Figure 3:
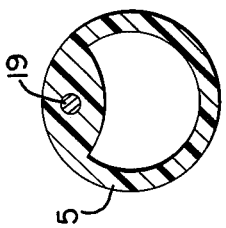
FIG. 3 is a cross-sectional view of inner tube 5.

In FIGS. 1 and 2, there is shown a surgical suction device 1 according to the principles of the present invention which is adapted to be connected to a suction pump (not shown) by a hose pipe 2. The surgical suction device 1 includes a handle 3 in the shape of a tube having a connector 4 connected, by gluing or otherwise, to one end of the suction device 1, and hose pipe 2 can be drawn onto or connected to connector 4. The connector 4 tapers in a direction away from handle 3 so that it may be connected to pipes having different dimensions and is also provided with annular steps or grooves in order to securely retain the hose pipe. A single tube suction device 5 (type Yankhauer) protrudes from the opposite end of handle 3. The device 5 includes a flexible plastic tube reinforced with a metal wire 19 which is substantially non-flexible, so that the tube 5 may be bent into a desired shape and will retain its new shape after bending.

The surgical suction device 1 also includes a sump suction device 6 (Rissler type-double tube) telescoped over the single tube suction device 5. The suction device 6 includes a rear pipe 7 closely fitting over handle 3 and a flexible tube 8 fastened to pipe 7 and having an outer diameter smaller than the inner diameter of pipe 7. A seal ring 9 is placed between pipe 7 and tube 8. The tube 8 includes at one end thereof a plurality of large and/or small openings 10 which openings are in communication with a space 11 formed between single tube suction device 5 and sump suction device 6. At the front end of the sump suction device 6, there is a tapered section 12 in the form of a separate piece of tube 12′. The tube 12′ is inserted a short distance into tube 8 and is fixed thereto by a suitable adhesive. The outer diameter of tube 12′ is substantially the same size as the inner diameter of flexible tube 8. The front end of tube 12′ is formed with a single tube suction opening 13, and the rear end or inner section is formed with a seat member 14 closely surrounding the tip of single tube suction device 5.

The single tube suction device 5 extends a short distance into the handle 3 and is fixedly connected thereto by a holder means 15 having substantially the same shape as connector 4. The handle 3 is provided with an aperture 16 for controlling the suction function and is located a short distance from mouth 17 of single tube suction device 5 in the handle 3. Such a location of aperture 16 prevents sprinkles of blood, etc., from hitting the person holding the surgical suction device 1. The pipe 7 of sump suction device 6 is also provided with an aperture 18 which is normally aligned with the aperture 16 in handle 3. Sump suction device 6 is rotatable in relation to handle 3 so that apertures 16, 18 can be displaced in relation to each other. The suction function is controlled by a person holding his finger over apertures 16, 18 which, as shown in FIG. 1, are aligned with each other. If the surgical suction device 1 gets stuck in the operation wound, the device 1 is released by removing the finger from apertures 16, 18. The apertures 16, 18 are in their aligned position when surgical suction device 1 is used as a single tube suction device. In this position, sump suction device 6 is in a position totally displaced over single tube suction device 5, and the front or tip of suction device 5 cooperates and is in contact with seat member 14.

A sump suction function is obtained if sump suction device 6 is in a position not completely displaced over single tube suction device 5. In such position, the tip of suction device 5 is spaced from seat member 14. When the surgical suction device of the present invention is used as a sump suction device, apertures 16, 18 are displaced relative to each other and are not in alignment. As a result, it is not necessary for a person to place his fingers over apertures 16, 18 of the surgical suction device 1.

In addition, as the front portion of surgical suction device 1 can be deformed into a new shape and retain its new shape, the surgical suction device of the present invention can easily be fastened to the place of operation.

The tip of suction device 5 can be provided with different types of caps and nozzles for different purposes when the sump suction device 6 has been removed. For example, Yankhauer tips, suction tips, flat tips, and outer perforated tubings may be employed.

In view of the foregoing, it should be clear that the surgical suction device 1 of the present invention may function either as a single tube suction device or a sump suction device. The open tip of single tube suction device 5 is movable into and out of contact with seat member 14 so that when the tip and seat member are in contact with each other, a single tube suction function is obtained, and when the tip and seat member are out of contact with each other, a sump suction function is obtained. When the device is operating as a single tube suction device, fluid is sucked into the device through suction opening 13 and passes through inner tube 5 and handle 3 on the way to the suction pump. When the surgical suction device 1 is operating as a sump suction device, fluid is sucked in by suction opening 13, as well as openings 10, and the fluid from the wound passes into inner tube 5, via space 11 for quickly removing large quantities of fluid from the wound.

A latitude of modification, change and substitution is intended in the foregoing disclosure and, in some instances, some features of the invention will be employed without a corresponding use of other features. Accordingly, it is appropriate that the appended claims be construed broadly and in a manner consistent with the spirit and scope of the invention herein.

What is claimed is:

1. A surgical suction device for removing fluid from a wound and adapted to be connected to a suction pump by a hose pipe, said device comprising:
   a tubular-shaped handle,
   an inner tube extending from one end of said handle and having a suction opening at one end thereof and a tip at the other end thereof,
   an outer tube surrounding said inner tube to form an annular space therebetween, said inner and outer tubes being movable relative to each other,
   a plurality of openings formed in said channel for quickly removing large quantities of fluid from a wound,
   said outer tube including at one end thereof a tapered section having a suction opening at one end and a seat member at its other end, and
   the tip of said inner tube being movable into and out of contact with said seat member so that when said tip and said seat member are in contact with each other, a single tube suction function is obtained in that suction is applied only to said tip, and when said tip and said seat member are out of contact with each other, a sump suction function is obtained in that suction is applied to both said plurality of openings and said tip.

2. A surgical suction device in accordance with claim 1 wherein said outer tube includes a pipe surrounding said handle and a flexible tube connected to said handle, said flexible tube having an outer diameter which is smaller than the inner diameter of said pipe.

3. A surgical suction device in accordance with claim 2 wherein said tapered section is formed in one piece, the outer diameter thereof being substantially equal in size to the inner diameter of said flexible tube, said tapered section being fixedly connected to and extending into a portion of said flexible tube.

4. A surgical suction device in accordance with claim 1 wherein said inner tube includes a flexible tube reinforced with a non-flexible wire so that said inner tube may be deformed and retain its new shape.

5. A surgical suction device in accordance with claim 1 wherein said handle includes an aperture for controlling the suction opening of said inner tube, said outer tube being telescoped over a portion of said handle and including an aperture normally aligned with said handle aperture.

6. A surgical suction device in accordance with claim 5 wherein said outer tube is constructed and arranged to be rotatable relative to said handle to displace said handle aperture relative to said outer tube aperture and thereby control the suction functions.

7. A surgical suction device in accordance with claim 1 wherein said tubular handle includes a connector formed at one end thereof.

8. A surgical suction device in accordance with claim 1 wherein said inner tube is constructed and arranged to extend into said handle.

9. A surgical suction device in accordance with claim 1 wherein said inner tube is of a smaller diameter than the diameter of said handle.

10. A surgical suction device in accordance with claim 1 wherein said inner tube includes means for holding said inner tube relative to said outer tube.

* * * * *